(12) United States Patent
Sun et al.

(10) Patent No.: US 12,131,833 B2
(45) Date of Patent: Oct. 29, 2024

(54) DEVICE FOR TREATING URANIUM TAILINGS WITH MICROORGANISM

(71) Applicant: The Fourth Research and Design Engineering Institute of China National Nuclear Corporation, Shijiazhuang (CN)

(72) Inventors: Juan Sun, Shijiazhuang (CN); Yifu An, Shijiazhuang (CN); Yang Gao, Shijiazhuang (CN); Guoxi Lian, Shijiazhuang (CN); Xuyang Wu, Shijiazhuang (CN); Haoyan Zhang, Shijiazhuang (CN)

(73) Assignee: The Fourth Research and Design Engineering Institute of China National Nuclear Corporation, Shijiazhuang (CN)

( * ) Notice: Subject to any disclaimer, the term of this patent is extended or adjusted under 35 U.S.C. 154(b) by 0 days.

(21) Appl. No.: 18/619,120

(22) Filed: Mar. 27, 2024

(65) Prior Publication Data
US 2024/0331887 A1      Oct. 3, 2024

Related U.S. Application Data

(63) Continuation of application No. PCT/CN2023/143296, filed on Dec. 29, 2023.

(30) Foreign Application Priority Data

Mar. 30, 2023   (CN) .......................... 202310329797.9

(51) Int. Cl.
*G21F 9/18* (2006.01)
*B09B 3/30* (2022.01)
(Continued)

(52) U.S. Cl.
CPC .................. *G21F 9/18* (2013.01); *B09B 3/30* (2022.01); *B09B 3/60* (2022.01); *C02F 3/00* (2013.01);
(Continued)

(58) Field of Classification Search
CPC ......... G21F 9/18; C12M 29/06; C12M 41/14; C02F 3/00; C02F 9/00; C02F 2103/16;
(Continued)

(56) References Cited

FOREIGN PATENT DOCUMENTS

CN       211660733 U     10/2020

OTHER PUBLICATIONS

English translation copy of Chinese Patent Publication No. CN 211660733U (2020).*

* cited by examiner

*Primary Examiner* — John Kim

(57) ABSTRACT

A device for treating uranium tailings with microorganism is provided and includes a treatment container, a spray water distribution assembly, a microbial incubator and a first pump. The water is transported from the microbial incubator to the spray water distribution assembly through the first pump, allowing the microorganisms to enter the interior of the uranium tailings in the treatment container. After treatment is completed, the water is collected by the water collection cylinder and sent back to the microbial incubator for recovery, so as to reduce the waste of microorganisms. The even distribution of horizontal spray pipes can evenly spray water containing microorganisms on the uranium tailings in the treatment container, which makes the distribution of microorganisms in the uranium tailings more uniform and can prevent inadequate treatment and improve the treatment efficiency of microorganisms on uranium tailings.

7 Claims, 3 Drawing Sheets

(51) Int. Cl.
*B09B 3/60* (2022.01)
*C02F 3/00* (2023.01)
*C02F 9/00* (2023.01)
*C12M 1/00* (2006.01)
*C02F 103/16* (2006.01)

(52) U.S. Cl.
CPC ............... *C02F 9/00* (2013.01); *C12M 29/06* (2013.01); *C12M 41/14* (2013.01); *C02F 2103/16* (2013.01); *C02F 2201/002* (2013.01); *C02F 2203/002* (2013.01); *C02F 2203/006* (2013.01)

(58) Field of Classification Search
CPC .......... C02F 2201/002; C02F 2203/002; C02F 2203/006; B09B 3/30; B09B 3/60
See application file for complete search history.

DEVICE FOR TREATING URANIUM TAILINGS WITH MICROORGANISM

TECHNICAL FIELD

The disclosure relates to the technical field of treatment of uranium tailings, and particularly to a device for treating uranium tailings with microorganism.

BACKGROUND

At present, the treatment of uranium tailings can be carried out through microbial remediation. The microbial remediation mainly involves screening and cultivating microorganisms that have biological adsorption, biological reduction, and biological mineralization effects on uranium, so that oxidized and dissolved uranium in the uranium tailings can be transformed into reduced uranium in a solid state, it exists in a form similar to crystalline uranium ore or pitchblende, and the reduced uranium is no longer continuously leached and migrated into seepage water. The concentration of pollutants in the seepage water is reduced by treating tailings. In addition, sedimentary uranium particles and constantly proliferating microorganisms can play a role in encapsulating and filling the tailings, which reduces the porosity of the tailings and prevents rainfall from entering the tailings, thereby reducing the amount of water seepage and achieving a dual effect of quantity reduction and quality improvement. However, most of the existing devices for treating uranium tailings with microorganisms have the problem of uneven distribution of microorganisms in the uranium tailings, resulting in poor treatment efficiency and low treatment efficiency of microorganisms in the uranium tailings treatment process.

SUMMARY

The objective of the disclosure is to provide a device for treating uranium tailings with microorganism, aimed at solving existing problems To achieve the above objective, a device for treating uranium tailings with microorganism is provided.

The device for treating uranium tailings with microorganism includes a treatment container, a spray water distribution assembly, a microbial incubator and a first pump. A top of the treatment container defines a feeding port configured to add the uranium tailings into the treatment container, the treatment container is provided with a water collection cylinder therein, and the water collection cylinder extends along a depth direction of the treatment container. The spray water distribution assembly is disposed on the top of the treatment container. The spray water distribution assembly includes a main frame body composed of multiple main pipe bodies connected end to end and multiple horizontal spray pipes disposed in the main frame body, two ends of each of the multiple horizontal spray pipes are respectively connected to corresponding two of the multiple the main pipe bodies, and each of the main frame body and the multiple horizontal spray pipes defines multiple spraying holes. The microbial incubator is configured to incubate microorganism. An input end of the microbial incubator is connected with a bottom of the water collection cylinder, an output end of the microbial incubator is connected with the spray water distribution assembly. The first pump is disposed on a pipeline between the microbial incubator and the spray water distribution assembly.

In an embodiment, a buffer collection container is disposed between the input end of the microbial incubator and the bottom of the water collection cylinder. And a second pump is disposed on a pipeline between an output end of the buffer collection container and the input end of the microbial incubator.

In an embodiment, the spray water distribution assembly further includes a vertical main pipe, multiple vertical spray pipes disposed inside the treatment container and extending along the depth direction of the treatment container, multiple connecting pipe bodies disposed between the vertical main pipe and the multiple vertical spray pipes. Each of the multiple vertical spray pipes defines multiple spraying holes distributed at equal intervals along a length direction of the vertical spray pipe.

In an embodiment, the microbial incubator includes a main container configured to contain a liquid and a feeding mechanism disposed at a side of the main container, and the feeding mechanism is configured to add microbial agents or nutrients into the main container.

In an embodiment, the feeding mechanism includes a main box body, a water supply pipeline, a drainage pipeline, a material box, and a sealing cover plate. The main box body is disposed at an outside of the main container and defines an opening at a side of the main box body, and the water supply pipeline is connected to a top of the main box body. A first end of the drainage pipeline is connected with a bottom of the main box body and a second end of the drainage pipeline is disposed inside the main container. The material box is disposed in the main box body and slidably connected to the main box body, a first end of the material box is disposed outside the main box body, and a second end of the material box is disposed inside the main box body. The sealing cover plate is disposed at the first end of the material box and configured to seal the opening of the main box body after an installation of the material box.

In an embodiment, the feeding mechanism further includes: a compression cover plate disposed at the opening of the main box body, and the compression cover plate is configured to compress the sealing cover plate, an end of the compression cover plate is hinged on the side of the main box body, and another end of the compression cover plate is detachably connected to the side of the main box body.

In an embodiment, the feeding mechanism further includes: a pushing block and an elastic flip plate, the second end of the material box is further hinged with the elastic flip plate, a top of the elastic flip plate protrudes from the material box, and the pushing block is disposed on an inner wall of the main box body and configured to drive the elastic flip plate to rotate.

In an embodiment, the second end of the drainage pipeline is disposed on a bottom of the main container, and the discharge assembly is disposed at the second end of the drainage pipeline.

In an embodiment, the discharge assembly includes multiple discharge pipe bodies disposed in a horizontal direction. The multiple discharge pipe bodies are radially wound around the drainage pipeline, and each of the multiple discharge pipe bodies defines multiple drainage holes configured to output water.

In an embodiment, a side of the treatment container is provided with observing windows and defines a waste discharge port configured for discharging the uranium tailings.

The beneficial effects of the device for treating the uranium tailings with the microorganism provided by the disclosure are as follows. Compared with the related art, the disclosure provides the water collection cylinder inside the treatment container and the spray water distribution assembly inside the treatment container, and then the output end of the microbial incubator is connected to the spray water distribution assembly through the pipelines. Therefore, the water containing sufficient microorganisms in the microbial incubator can be transported to the spray water distribution assembly through the first pump. In addition, the spray water distribution assembly includes a main frame body composed of the multiple main pipe bodies connected end to end and multiple horizontal spray pipes disposed in the main frame body, and two ends of each of the multiple horizontal spray pipes are respectively connected to corresponding two of the multiple main pipe bodies, and each of the main frame body and the multiple horizontal spray pipes defines multiple spraying holes. During treatment of uranium tailings, the uranium tailings are added into the treatment container through the feeding port on the top of the treatment container, and then the water is transported from the microbial incubator to the spray water distribution assembly through the first pump, allowing the microorganisms to enter the interior of the uranium tailings in the treatment container. After treatment is completed, the water is collected by the water collection cylinder and sent back to the microbial incubator for recovery, so as to reduce the waste of microorganisms. Moreover, the spray water distribution assembly includes the main frame body and the multiple horizontal spray pipes, which can cover the entire top of the treatment container. The even distribution of horizontal spray pipes can evenly spray water containing microorganisms on the uranium tailings in the treatment container, which makes the distribution of microorganisms in the uranium tailings more uniform and can prevent inadequate treatment and improve the treatment efficiency of microorganisms on uranium tailings.

BRIEF DESCRIPTION OF DRAWINGS

In order to provide a clearer explanation of the technical solution in the embodiments of the disclosure, a brief introduction will be given below to the attached drawings required in the embodiments or related art descriptions. It is evident that the attached drawings in the following description are only some embodiments of the disclosure. For those skilled in the art, other attached drawings can be obtained based on these drawings without creative labor.

DESCRIPTION OF REFERENCE SIGNS 1. treatment container; 101. feeding port; 11. observing window; 12. waste discharge port; 2. spray water distribution assembly; 21. main frame body; 201. vertical main pipe; 211. main pipe body; 22. horizontal spray pipe; 23. vertical spray pipe; 3. microbial incubator; 31. main container; 32. feeding mechanism; 321. main box body; 322. material box; 323. sealing cover plate; 324. compression cover plate; 325. elastic flip plate; 326. pushing block; 33. water supply pipeline; 34. drainage pipeline; 35. discharge assembly; 36. discharge pipe body; 4. first pump; 43. pipeline; 5. buffer collection container; 56. pipeline; 6. second pump; 7. water collection cylinder; 8. connecting pipe body; 9. spraying hole.

DETAILED DESCRIPTION OF EMBODIMENTS

In order to make the technical problems, technical solutions, and beneficial effects to be solved by the disclosure more clearly, the following will provide further detailed explanations of the disclosure in conjunction with the attached drawings and embodiments. It should be understood that the specific embodiments described here are only intended to explain the disclosure and are not intended to limit the disclosure.

Figure 1:
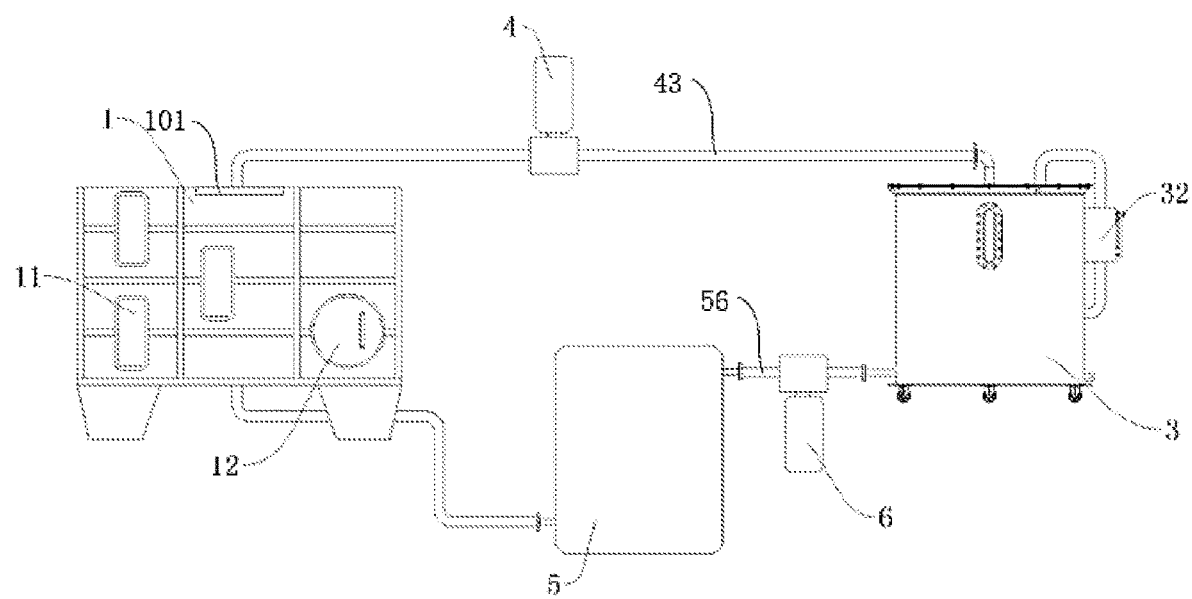
FIG. 1 illustrates a schematic structural diagram of a device for treating uranium tailings with microorganism in an embodiment of the disclosure.
Figure 2:
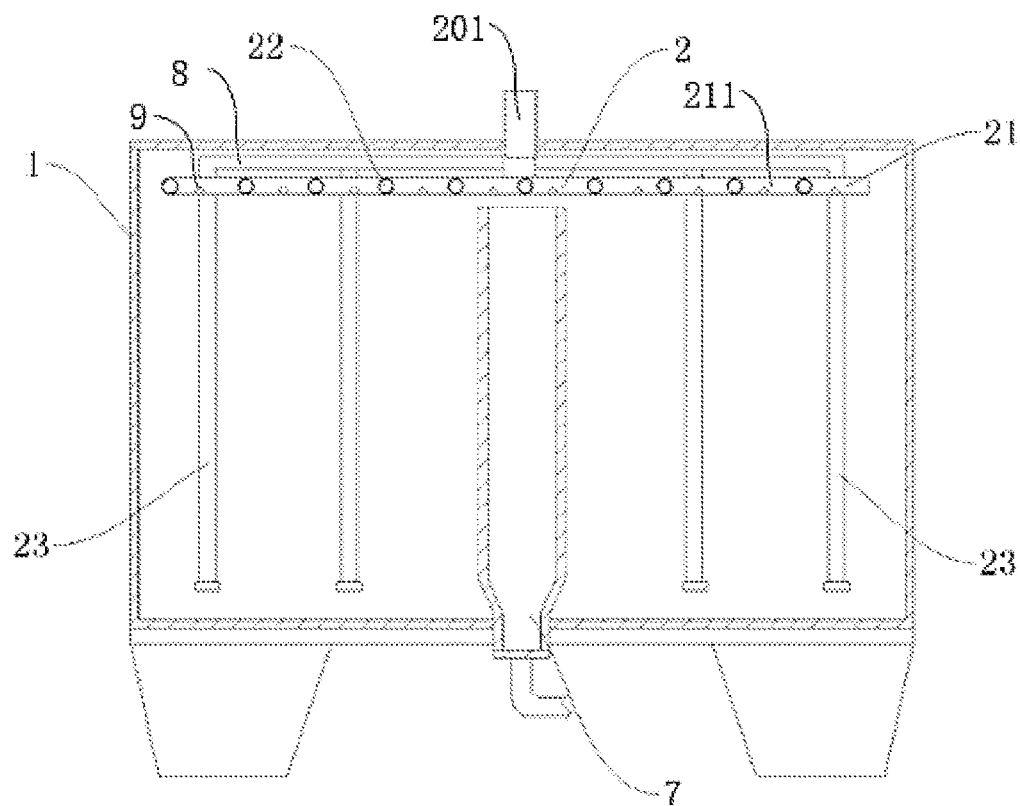
FIG. 2 illustrates a schematic cross-sectional diagram of a treatment container in the embodiment of the disclosure.

As shown in FIGS. 1 and 2, a device for treating uranium tailings with microorganism is provided and includes a treatment container 1, a spray water distribution assembly 2, a microbial incubator 3 and a first pump 4. A top of the treatment container 1 defines a feeding port 101 configured to add the uranium tailings into the treatment container 1, the treatment container 1 is provided with a water collection cylinder 7 therein, and the water collection cylinder 7 extends along a depth direction of the treatment container 1. The spray water distribution assembly 2 is disposed on the top of the treatment container 1. The spray water distribution assembly 2 includes a main frame body 21 composed of multiple main pipe bodies 211 connected end to end and, and multiple horizontal spray pipes 22 disposed in the main frame body 21. Two ends of each of the multiple horizontal spray pipes 22 are respectively connected to corresponding two of the multiple the main pipe bodies 211, each of the main frame body 21 and the multiple horizontal spray pipes defines multiple spraying holes 9. The microbial incubator 3 is configured to incubate the microorganism. An input end of the microbial incubator 3 is connected with a bottom of the water collection cylinder 7, and an output end of the microbial incubator 3 is connected with the spray water distribution assembly 2. The first pump 4 is disposed on a pipeline 43 between the microbial incubator 3 and the spray water distribution assembly 2.

Figure 4:
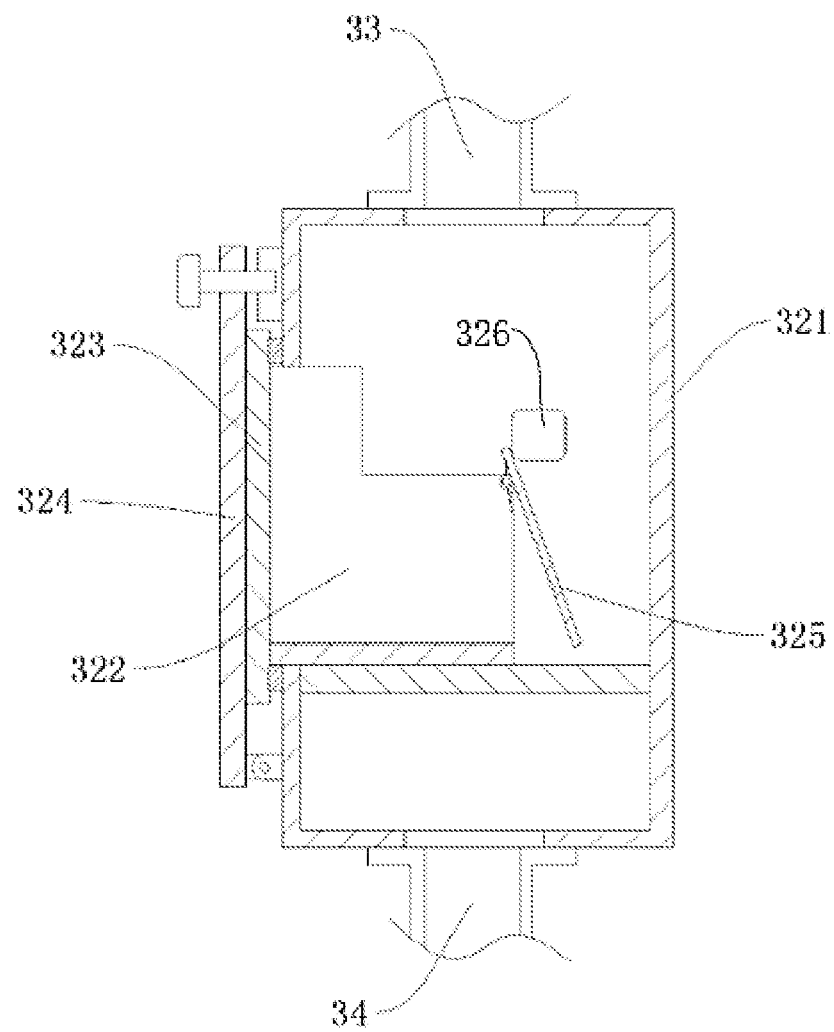
FIG. 4 illustrates a schematic structural diagram of a feeding mechanism in the embodiment of the disclosure.

Compared with related art, the device of the disclosure provides the water collection cylinder 7 inside the treatment container 1 and the spray water distribution assembly 2 inside the treatment container 1, and the output end of the microbial incubator 3 is connected to the spray water distribution assembly 2 through the pipeline 43. Therefore, the water containing sufficient microorganisms in the microbial incubator 3 can be transported to the spray water distribution assembly 2 through the first pump 4. In addition, the spray water distribution assembly 2 includes the main frame body 21 composed of the main pipe bodies 211 connected end to end and the multiple horizontal spray pipes 22 disposed in the main frame body 21, and two ends of each of the multiple horizontal spray pipes 22 are respectively connected to corresponding two of the multiple the main pipe bodies 211. Each of the main frame body 21 and the multiple horizontal spray pipes 22 defines the multiple spraying holes 9. During the treatment of uranium tailings, the uranium tailings are added into the treatment container 1 through the feeding port 101 defined on the top of the treatment container 1, and then the water is transported from the microbial incubator 3 to the spray water distribution assembly 2 through the first pump 4, allowing the microorganisms to enter the interior of the uranium tailings in the treatment container 1. After the treatment is completed, the water is collected by the water collection cylinder 7 and sent back to the microbial incubator 3 for recovery, so as to reduce the waste of the microorganisms. Moreover, the spray water distribution assembly 2 includes the main frame body 21 and the multiple horizontal spray pipes 22, which can cover the entire top of the treatment container 1. The even distribution of horizontal spray pipes 22 can evenly spray water containing microorganisms on the uranium tailings in the treatment container 1, which makes the distribution of the microorganisms in the uranium tailings more uniform and can prevent inadequate treatment and improve the treatment efficiency of microorganisms on uranium tailings.

It should be noted that the water collection cylinder 7 can be made of a permeable material or defines small holes on a side wall of the collection cylinder 7 that allow only water to pass through to facilitate the collection of water from the tailings into the water collection cylinder 7. The water collection cylinder 7 is disposed in a center of the treatment container 1. After the uranium tailings are laid flat in the treatment container 1, the uranium tailings can flow naturally to form a water flow angle of 1%-1.5% with a slope of a collection pipe (i.e. water collection cylinder 7), allowing the water in the uranium tailings to better penetrate into the water collection cylinder 7.

In an embodiment, as shown in FIGS. 1-2, a buffer collection container 5 is disposed between the input end of the microbial incubator 3 and the bottom of the water collection cylinder 7, and a second pump 6 is disposed on a pipeline 56 between an output end of the buffer collection container 5 and the input end of the microbial incubator 3. Specifically, the setting of the buffer collection container 5 can temporarily accommodate the water discharged from the bottom of the water collection cylinder 7, and then the water separated from the uranium tailings is re-added into the microbial incubator 3 through the second pump 6. It is possible to separate the water from the tailings particles in the water by standing still, which can achieve the recovery of residual microorganisms and significantly reduce the overall microbial culture medium and injection volume.

In a specific embodiment, inner walls of the buffer collection container 5 and the treatment container 1 are both coated with an epoxy resin anti-corrosion coating with a thickness 2-5 centimeters (cm). After 48 hours of the coating, the epoxy resin anti-corrosion coating is air dried to form a protective layer before use.

To have a better spraying effect, as shown in FIGS. 1-2, the spray water distribution assembly 2 further includes a vertical main pipe 201, multiple vertical spray pipes 23 disposed inside the treatment container 1 and extending along the depth direction of the treatment container 1, connecting pipe bodies 8 disposed between the vertical main pipe 201 and the multiple vertical spray pipes 23, and each of the multiple vertical spray pipes 23 defines multiple spraying holes 9 distributed at equal intervals along a length direction of the vertical spray pipe 23. Specifically, the multiple vertical spray pipes 23 extend along the depth direction of the treatment container 1, and are distributed at an equal interval inside the treatment container 1. The water containing microorganisms is added into the vertical spray pipes 23 through the vertical main pipe 201 and the connecting pipe bodies 8. The setting of the vertical spray pipes 23 can make the adding of the water containing microorganisms into the tailings more uniform. After adding the uranium tailings, a BN-30 single person backpack drill can be used to construct holes in the uranium tailings first, and then the vertical spray pipes 23 can be vertically inserted into the holes of the uranium tailings.

In a specific embodiment, conical blocks are disposed at the bottoms of the vertical spray pipes 23, which can facilitate the insertion of the vertical spray pipes 23 into the interior of the uranium tailings. In addition, the vertical main pipe 201 and the horizontal spray pipes 22 can be connected with the same external pipelines. In another embodiment, the horizontal spray pipes 22 and the main frame body 21 can also be connected to the external pipelines using a pipe body independent from the vertical main pipe 20.

In an embodiment, as shown in FIGS. 1-2, the microbial incubator 3 includes a main container 31 configured to contain a liquid and a feeding mechanism 32 disposed at a side of the main container 31, the feeding mechanism 32 is configured to add microbial agents or nutrients into the main container 31. Specifically, the main container 31 is configured to accommodate the culture medium and microbial agents, and to achieve the cultivation of the microorganisms. In addition, the feeding mechanism 32 is disposed at the side of the main container 31, which can facilitate the addition of microbial agents or nutrients to the main container 31, making the use of microbial incubator 3 more convenient.

The feeding mechanism 32, as shown in FIG. 3, includes a main box body 321, a material box 322, a sealing cover plate 323, a water supply pipeline 33 and a drainage pipeline 34. The main box body 321 is disposed at an outside of the main container 31 and defines an opening at a side of the main box body 321, the water supply pipeline 33 is connected to a top of the main box body 321. A first end of the drainage pipeline 34 is connected with a bottom of the main box body 321 and a second end of the drainage pipeline 34 is disposed inside the main container 31. The material box 322 is disposed in the main box body 321 and slidably connected to the main box body 321, a first end of the material box 322 is disposed outside the main box body 321, and a second end of the material box 322 is disposed inside the main box body 321. The sealing cover plate 323 is disposed at the first end of the material box 322 and configured to seal the opening of the main box body 321 after an installation of the material box 322. Specifically, the water supply pipeline 33 at the top of the main box body 321 can be connected to an external water source or internally connected to the main container 31, and the water can be extracted into the main box body 321 through a third pump. When it is necessary to add microbial agents or nutrients to the main container 31, the material box 322 can be pulled out and microbial agents or nutrients can be placed inside the material box 322. Then, the material box 322 can be pushed into the main box body 321, thus the water can be injected into the main box body 321 through the water supply pipeline 33 to flush the microbial agents or nutrients from the material box 322 to the bottom of the main box body 321, and the microbial agents or nutrients enter the interior of the main box body 321 through the drainage pipeline 34, making it more convenient to add materials to the main container 31.

In addition, the sealing cover plate 323 is disposed at the first end of the material box 322. When the material box 322 is inserted into the main box body 321, the sealing cover plate 323 can be abut against the side of the main box body 321 to seal the opening, ensuring the sealing of the main box body 321. Moreover, a sealing ring is further disposed on the side of the sealing cover plate 323 to improve the sealing.

In an embodiment, support slides are disposed on the side walls of the main box body 321 configured for supporting material box 322, which can make the sliding of material box 322 more convenient. The support slides are disposed on two sides of the material box 322.

To have a better sealing performance, as shown in FIG. 4, a compression cover plate 324 is disposed at the opening of the main box body 321 and configured to compress the sealing cover plate 323, an end of the compression cover plate 324 is hinged on a side of the main box body 321, and another end of the compression cover plate 324 is detachably connected to the side of the main box body 321. Specifically, after the material box 322 is disposed in place, the compression cover plate 324 can be flipped and pressed against the side of the sealing cover plate 323. Then, the other end of the compression cover plate 324 can be fixed to the side of the main box body 321 through a fastener, making the sealing cover plate 323 more tightly abut against the side of the main box body 321, thereby improving the sealing at the opening of the side of the main box body 321 and making the use of material box 322 safer.

In an embodiment, as shown in FIG. 4, the second end of the material box 322 is further hinged with an elastic flip plate 325, a top of the elastic flip plate 325 protrudes from the material box 322, and a pushing block 326 is disposed on an inner wall of the main box body 321 and configured to drive the elastic flip plate 325 to rotate. Specifically, the second end of the material box 322 defines an opening, and the elastic flip plate 325 is hinged on the upper part of the material box 322 through a rotating shaft. An elastic torsion spring is provided between the material box 322 and the elastic flip plate 325, and the elastic torsion spring is sheathed outside the rotating shaft. When the material box 322 is pulled out, which drives the elastic flip plate 325 in the main box body 321 to rotate, and the elastic flip plate 325 can be pressed against the opening to maintain a seal under the action of the elastic torsion spring. When the material box 322 is disposed in place inside the main box body 321, the top of the elastic flip plate 325 will flip under the action of the pushing block 326, thereby opening the opening of the material box 322, so that the materials inside the material box 322 can flow out conveniently after being impacted.

In an embodiment, as shown in FIGS. 1-2, the second end of the drainage pipeline 34 is disposed on a bottom of the main container 31, and the discharge assembly 35 is disposed at the second end of the drainage pipeline 34. The setting of the discharge assembly 35 can make the distribution of microbial agents or nutrients passing through the feeding mechanism 32 more uniform in the main container 31.

Figure 3:
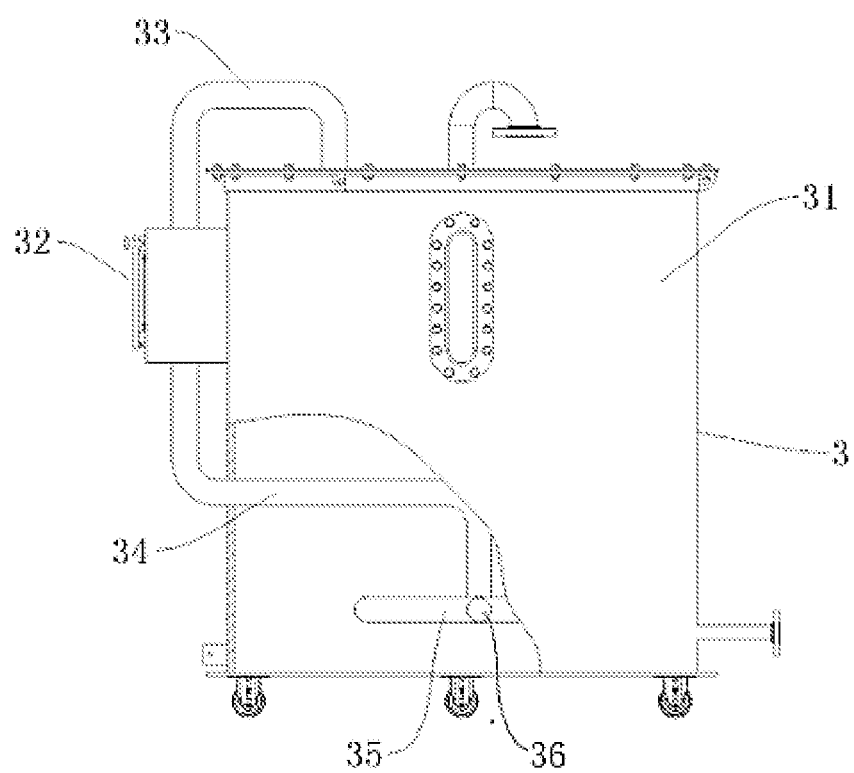
FIG. 3 illustrates a schematic structural diagram of a microbial incubator in the embodiment of the disclosure.

The discharge assembly 35 as shown in FIG. 3 includes multiple discharge pipe bodies 36 disposed in a horizontal direction, the multiple discharge pipe bodies 36 are radially are wound around the drainage pipeline 34, and each of the multiple discharge pipe bodies 36 defines multiple drainage holes configured to output water. Specifically, the multiple discharge pipe bodies 36 can be distributed radially along the main container 31, allowing the material to be distributed to various parts of the main container 31.

In an embodiment, as shown in FIG. 1, a side of the treatment container 1 is provided with observing windows 11 and defines a waste discharge port 12 configured for discharging the uranium tailings, which can make it more convenient to observe and handle the interior of the treatment container 1.

A treatment method for uranium tailings using the device is as follows.

Addition and standing of uranium tailings: firstly, the uranium tailings are poured into the treatment container 1 through the feeding port 101 at the top of the treatment container 1, and then the uranium tailings are stood still for 24-48 hours to allow the uranium tailings to deposit naturally.

Microbial cultivation: microbial strains and certain nutrients are added into the microbial incubator 3, with a controlled inoculation amount of 1-1.5%. After adding an appropriate amount of microbial nutrients, the microbial strains grow naturally outdoors for 3-5 days. The reducing activity of microorganisms is qualitatively analyzed in the water using an acetic acid test paper after the growth, with an aim of the test paper turning black as the cultivation endpoint. After the activity is qualified in the microbial incubator 3, the next step of operation is processed.

Microbial injection: the first pump 4 is controlled through a control unit, then microorganisms are injected from the microbial incubator 3 into the spray water distribution assembly 2 inside the treatment container 1. Through the spray water distribution assembly 2, the water containing microorganisms is evenly sprayed throughout the uranium tailings, and the water collected by the water collection cylinder 7 is discharged.

The spray pipes and the water supply pipes are both made of DN40PP material, the horizontal spacing between every adjacent two holes on the spray pipes or the water supply pipes is 10 millimeters (mm), and the vertical spacing between every adjacent two holes on the spray pipes or the water supply pipes is 20 mm, and each hole on the spray pipes or the water supply pipes is evenly drilled with a diameter of about 1-2 mm. By constructing a constant flow pump to continuously inject microbial agents into the DN40PP material pipelines, a flow rate can be controlled at 2-4 cubic meters per hour ($m^3/h$). The spraying water distribution assembly 2 is connected to a surface uniform water replenishment spraying device or a deep liquid injection pipeline device, or a combination of the surface uniform water replenishment spraying device and the deep liquid injection pipeline device (FIG. 3). And holes on the surface of uranium tailings need to be pre-drilled with the BN-30 single person backpack drill before the vertical spray pipes 23 are vertically inserted into the holes. When spraying or injecting microbial agents, the total amount of the microbial agents injected into each treatment container should be controlled at 1-1.2 tons per time. During this period, attention should be paid to the permeability of the microbial agents, and the moisture content of the surface uranium tailings from 0-20 cm should be maintained at 80-90%. The microbial agents should be controlled to have almost no water surface or the water surface should not exceed 2 cm, thereby reducing the duration of contact between the microbial agents and the air. After infiltration through the pores of the uranium tailings, the microbial agents flowing out from the bottom of the water collection cylinder 7 in the spray water distribution assembly 2 flow into a polyethylene recovery bucket with 0.5 cubic meters ($m^3$) through the pipeline with the same material. The recovery bucket serves as the buffer collection container 5, providing water quality precipitation and the recovery of residual microbial agents. The residual microbial agents in the recovery bucket are filled back into the original microbial culture bucket using a DN40PP material pipeline and a constant flow pump to collect the residual microbial agents. The liquid injection cycle of each container is controlled within 5-7 days. After each injection, a certain amount of microbial culture medium is added to the microbial incubator 3 for secondary cultivation, thereby forming a coherent microbial source control system. The buffer collection container 5 defines an outlet, and the water flowing from the outlet of the buffer collection container 5 is regularly monitored. Water quality indicators such as potential of hydrogen (pH) value, dissolved oxygen (DO) value, unit (U) mass concentration, and microbial indicators such as optical density 600 (OD600) and 16S ribosomal ribonucleic acid (rRNA) are regularly monitored in the water. After the U mass concentration of the water drops below 0.3 milligrams per liter (mg/L) for 1-3 consecutive weeks and the difference in the U mass concentrations is less than 15%, the restoration is judged to be completed. The device can be reused. After the first batch of tailings meets the standards, the opening can be opened, and the repaired tailings can be transported out by manual or tracked transportation. The new tailings to be treated can be filled and treated with the recycled microbial agents in the treatment container 1 for secondary treatment.

The above are only specific embodiments of the disclosure and are not intended to limit it. Any amendments, equivalent substitutions, and improvements made within the spirit and principles of the disclosure shall be included within the scope of protection of the disclosure.

What is claimed is:

1. A device for treating uranium tailings with microorganism, comprising:
   a treatment container, wherein a top of the treatment container defines a feeding port configured to add the uranium tailings into the treatment container, the treatment container is provided with a water collection cylinder therein, and the water collection cylinder extends along a depth direction of the treatment container;
   a spray water distribution assembly, wherein the spray water distribution assembly is disposed on the top of the treatment container; wherein the spray water distribution assembly comprises: a main frame body composed of a plurality of main pipe bodies connected end to end and a plurality of horizontal spray pipes disposed in the main frame body, two ends of each of the plurality of horizontal spray pipes are respectively connected to corresponding two of the plurality of the main pipe bodies, and each of the main frame body and the plurality of the horizontal spray pipes defines a plurality of spraying holes; wherein the spray water distribution assembly further comprises: a vertical main pipe, a plurality of vertical spray pipes disposed inside the treatment container and extending along the depth direction of the treatment container, and a plurality of connecting pipe bodies disposed between the vertical main pipe and the plurality of vertical spray pipes; and each of the plurality of vertical spray pipes defines a plurality of spraying holes distributed at equal intervals along a length direction of the vertical spray pipe;
   a microbial incubator, configured to incubate the microorganism, wherein an input end of the microbial incubator is connected with a bottom of the water collection cylinder, an output end of the microbial incubator is connected with the spray water distribution assembly, the microbial incubator comprises: a main container configured to contain a liquid and a feeding mechanism disposed at a side of the main container, the feeding mechanism is configured to add microbial agents or nutrients into the main container, and the feeding mechanism comprises: a main box body, a material box, a pushing block and an elastic flip plate; the main box body is disposed at an outside of the main container and defines an opening at a side of the main box body, the material box is disposed in the main box body and slidably connected to the main box body, a first end of the material box is disposed outside the main box body, a second end of the material box is disposed inside the main box body and hinged with the elastic flip plate, a top of the elastic flip plate protrudes from the material box, and the pushing block is disposed on an inner wall of the main box body and configured to drive the elastic flip plate to rotate; and
   a first pump, disposed on a pipeline between the microbial incubator and the spray water distribution assembly.

2. The device as claimed in claim 1, further comprising:
   a buffer collection container, disposed between the input end of the microbial incubator and the bottom of the water collection cylinder; and
   a second pump, disposed on a pipeline between an output end of the buffer collection container and the input end of the microbial incubator.

3. The device as claimed in claim 2, wherein the feeding mechanism further comprises: a water supply pipeline connected to a top of the main box body, a sealing cover plate and a drainage pipeline; a first end of the drainage pipeline is connected with a bottom of the main box body and a second end of the drainage pipeline is disposed inside the main container; and the sealing cover plate is disposed at the first end of the material box and configured to seal the opening of the main box body after an installation of the material box.

4. The device as claimed in claim 3, wherein the feeding mechanism further comprises: a compression cover plate disposed at the opening of the main box body, and the compression cover is configured to compress the sealing cover plate, an end of the compression cover plate is hinged on the side of the main box body, and another end of the compression cover plate is detachably connected to the side of the main box body.

5. The device as claimed in claim 3, wherein the microbial incubator further comprises: a discharge assembly; and the second end of the drainage pipeline is disposed on a bottom of the main container, and the discharge assembly is disposed at the second end of the drainage pipeline.

6. The device as claimed in claim 5, wherein the discharge assembly comprises: a plurality of discharge pipe bodies disposed in a horizontal direction, the plurality of discharge pipe bodies are wound around the drainage pipeline, and each of the plurality of discharge pipe bodies defines a plurality of drainage holes configured to output water.

7. The device as claimed in claim 1, wherein a side of the treatment container is provided with observing windows and defines a waste discharge port configured to discharge the uranium tailings.

\* \* \* \* \*